United States Patent
Fan et al.

(10) Patent No.: US 9,814,439 B2
(45) Date of Patent: Nov. 14, 2017

(54) TISSUE MOTION COMPARISON DISPLAY

(75) Inventors: Liexiang Fan, Issaquah, WA (US); David E. Gustafson, North Bend, WA (US); John I. Jackson, Menlo Park, CA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 2674 days.

(21) Appl. No.: 11/039,251

(22) Filed: Jan. 19, 2005

(65) Prior Publication Data

US 2006/0173328 A1    Aug. 3, 2006

(51) Int. Cl.
- A61B 8/08 (2006.01)
- G01S 7/52 (2006.01)
- G01S 15/89 (2006.01)
- A61B 6/00 (2006.01)

(52) U.S. Cl.
CPC ........... *A61B 8/08* (2013.01); *G01S 7/52071* (2013.01); *G01S 15/8979* (2013.01); *A61B 6/503* (2013.01); *A61B 8/0883* (2013.01)

(58) Field of Classification Search
CPC ......... A61B 8/08; A61B 8/0883; A61B 6/503; G01S 7/52071; G01S 15/8979
USPC ....... 600/407, 437, 441, 443, 447, 453–455; 382/284; 128/916
See application file for complete search history.

(56) References Cited

U.S. PATENT DOCUMENTS

| | | | |
|---|---|---|---|
| 4,828,500 A * | 5/1989 | Seidel et al. | 434/247 |
| 5,285,788 A * | 2/1994 | Arenson et al. | 600/441 |
| 5,429,137 A * | 7/1995 | Phelps et al. | 600/455 |
| 5,562,448 A * | 10/1996 | Mushabac | 433/215 |
| 5,615,680 A * | 4/1997 | Sano | 600/437 |
| 5,664,571 A * | 9/1997 | Yamazaki | 600/441 |
| 5,800,356 A * | 9/1998 | Criton et al. | 600/441 |
| 5,882,306 A * | 3/1999 | Ramamurthy et al. | 600/440 |
| 5,961,462 A * | 10/1999 | Loupas et al. | 600/453 |
| 5,976,088 A * | 11/1999 | Urbano et al. | 600/443 |
| 6,015,384 A | 1/2000 | Ramamurthy et al. | |
| 6,030,344 A * | 2/2000 | Guracar et al. | 600/447 |
| 6,056,691 A * | 5/2000 | Urbano et al. | 600/443 |
| 6,086,537 A * | 7/2000 | Urbano et al. | 600/443 |
| 6,149,594 A * | 11/2000 | Rock | G01S 7/52098 600/437 |
| 6,193,660 B1 | 2/2001 | Jackson et al. | |
| 6,201,900 B1 * | 3/2001 | Hossack et al. | 382/294 |
| 6,228,030 B1 * | 5/2001 | Urbano et al. | 600/443 |
| 6,258,029 B1 | 7/2001 | Guracar et al. | |
| 6,511,426 B1 * | 1/2003 | Hossack et al. | 600/437 |
| 6,527,717 B1 * | 3/2003 | Jackson et al. | 600/437 |
| 6,590,999 B1 | 7/2003 | Comaniciu et al. | |
| 6,592,522 B2 * | 7/2003 | Bjaerum et al. | 600/443 |

(Continued)

OTHER PUBLICATIONS

"Robust Real-Time Myocardial Border Tracking for Echocardiography: An Information Fusion Approach," by Dorin Comaniciu, Senior Member, IEEE, Xiang Sean Zhou, and Sriram Krishnan; IEEE V.23, No. 7; Jul. 2004; pp. 549-560.

*Primary Examiner* — Bo J Peng

(57) ABSTRACT

A difference between a detected motion and a reference motion is automatically displayed. The reference motion is a modeled motion of an organ, a base line motion of an organ or another portion of an organ. A deviation in motion amplitude, angle or both angle and amplitude from a reference set may more easily identify abnormal or normal motion of the organ.

23 Claims, 1 Drawing Sheet

(56) References Cited

U.S. PATENT DOCUMENTS

| | | |
|---|---|---|
| 6,673,017 B1 | 1/2004 | Jackson |
| 6,674,879 B1* | 1/2004 | Weisman et al. ............. 382/128 |
| 7,194,145 B2* | 3/2007 | Avinash ....................... 382/284 |
| 7,454,048 B2* | 11/2008 | Schoisswohl et al. ....... 382/131 |
| 2003/0095121 A1 | 5/2003 | Huseyin et al. |
| 2003/0097068 A1* | 5/2003 | Hossack et al. ............. 600/443 |
| 2004/0064036 A1 | 4/2004 | Mao et al. |
| 2004/0136490 A1* | 7/2004 | Edic et al. ........................ 378/4 |
| 2004/0167395 A1* | 8/2004 | Behrenbruch et al. ....... 600/420 |
| 2004/0208341 A1 | 10/2004 | Zhou et al. |
| 2004/0254439 A1* | 12/2004 | Fowkes et al. ............... 600/407 |
| 2004/0254440 A1 | 12/2004 | Pedrizzetti et al. |
| 2004/0260346 A1* | 12/2004 | Overall et al. .................... 607/4 |
| 2005/0096543 A1* | 5/2005 | Jackson et al. ............... 600/441 |
| 2005/0124888 A1* | 6/2005 | Jjt Rein et al. ............... 600/443 |
| 2005/0187470 A1* | 8/2005 | Kubota et al. ................ 600/437 |
| 2005/0215897 A1* | 9/2005 | Sakaguchi et al. ........... 600/437 |
| 2006/0074309 A1* | 4/2006 | Bonnefous .................... 600/437 |
| 2007/0010743 A1* | 1/2007 | Arai ............................... 600/443 |
| 2008/0051652 A1* | 2/2008 | Ichioka et al. ................ 600/437 |
| 2009/0005679 A1* | 1/2009 | Dala-Krishna ............... 600/437 |

* cited by examiner

TISSUE MOTION COMPARISON DISPLAY

BACKGROUND

The present invention relates to displays of tissue motion. In particular, motion associated with organs or other tissues within a body is displayed for diagnostic use by a sonographer or other medical personnel.

The health of a heart may be diagnosed, at least in part, by assessing motion of the myocardial wall. For example, a series of two-or three-dimensional images showing motion of the myocardial wall is viewed. A medical practitioner makes a judgment about the health of the myocardial wall by mental comparison to motion associated with known defects or healthy wall motion. The medical practitioner may compare the sequence of images to an adjacent sequence of images showing either a healthy or unhealthy heart.

Wall motion is shown using one of various ultrasound modes. B-mode, Doppler mode, or both B-mode and Doppler mode imaging may be used for diagnosing myocardial wall motion. Other imaging modes or detection techniques provide additional information for diagnosis. For example, an amount of displacement or a ratio of displacements at two different times associated with a particular wall location may be determined and displayed. As another example, inward systole or outward diastole motion may be separately color-coded for more accurate identification of the two phases. Different colors are used for tissue in different positions. As yet another example, an amount of perfusion of contrast agent within the myocardial wall may be color-coded or otherwise displayed with an image to indicate the health of the heart, such as disclosed in U.S. Pat. No. 6,015,384, the disclosure of which is incorporated herein by reference.

BRIEF SUMMARY

By way of introduction, the preferred embodiments described below include methods, systems and computer-readable media with instructions for displaying tissue motion information. A difference between a detected motion and a reference motion is automatically displayed. The reference motion is a modeled motion, a base line motion or another portion of an organ. A deviation in motion amplitude, angle or both angle and amplitude from a reference may more easily identify abnormal or normal motion of the organ.

In a first aspect, a method is provided displaying tissue motion information. A first motion characteristic of tissue within a body is determined. The first motion characteristic is compared to a first reference motion characteristic. A difference is determined as a function of the comparison. Information is displayed as a function of the difference.

In a second aspect, a system is provided for displaying tissue motion information. A processor is operable to determine a first motion characteristic of tissue within a body, compare the first motion characteristic to a first reference motion characteristic, and determine a difference as a function of the comparison. A display is operable to display information as a function of the difference.

In a third aspect, a computer-readable storage medium is provided with stored data representing instructions executable by a programmed processor for displaying tissue motion information. The instructions include determining a first motion characteristic of tissue within a body with ultrasound data acquired at different times; comparing the first motion characteristic to a first reference motion characteristic; and determining a difference as a function of the comparison.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Organ motion is objectively and automatically compared relative to a reference. For example, the motion of a myocardial wall of the heart is compared to the reference motion using ultrasound or other medical imaging modalities. The reference motion may be generated from a dynamic model, such as a mathematical model, a database or combinations of both. Other reference motions may be derived from baseline images, examination of the same patient or from the same data but at a different location. The result of the comparison is displayed as either a dynamic sequence or a static image. The result may be qualitative, such as modulating a characteristic of a two-or three-dimensional display as a function of the comparison, or quantitative, such as displaying a numerical value or a graph. Other displays include identifying in which of a plurality of different ranges of differences the comparison is located.

Figure 1:
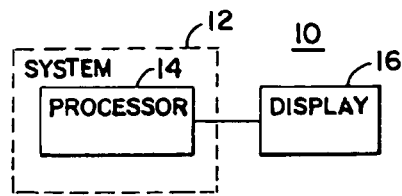
FIG. 1 is a block diagram of one embodiment of a system for displaying tissue motion information.

FIG. 1 shows a system 10 for displaying tissue motion information. The system 10 includes an imaging system 12 having a processor 14 and a display 16. Additional, different or fewer components may be provided. For example, the imaging system 12 is a medical diagnostic ultrasound system for real-time acquisition of ultrasound information. The medical diagnostic ultrasound imaging system 12 includes a transducer, beamformers, detectors and/or other components. As another example, the imaging system 12 is a workstation, personal computer or network for processing or otherwise generating displays of medical images. In yet other alternative embodiments, the imaging system 12 is a computed tomography system, a magnetic resonance system, an x-ray system, a positron emission system or other now known or later developed imaging modality.

The processor 14 is a general processor, digital signal processor, application-specific integrated circuit, field programmable gate array, analog circuit, network, combinations thereof or other now known or later developed devices for processing data. A plurality of devices for interacting to perform the same or different functions of the processor 14 discussed herein may be provided as the processor 14. The processor 14 is a control processor, a processor dedicated to generating tissue motion information, a processor within an imaging data path, a remote processor, three-dimensional image processor, or other processor with dedicated or multiple uses within the imaging system 12. The processor 14 is operable in response to stored instructions for generating tissue motion information. Stored instructions are firmware or software for controlling operation of the processor 14 as discussed below.

The processor 14 is operable to determine a motion characteristic of tissue within a body. For example, the motion of an organ, organ wall, vessel, valve or other tissue in one or more locations is determined. The tissue is in any body, such as a mechanical or biological body. The processor 14 receives data from a scan of the body at different times to identify a motion characteristic of the tissue. The processor 14 is operable to compare the determined motion characteristic to a reference motion characteristic. A difference is determined as a function of the comparison. An amount of difference between a detected motion and a reference motion indicates a deviation from the expected, desired or undesired motion. Deviations may provide diagnostically significant information.

Figure 2:
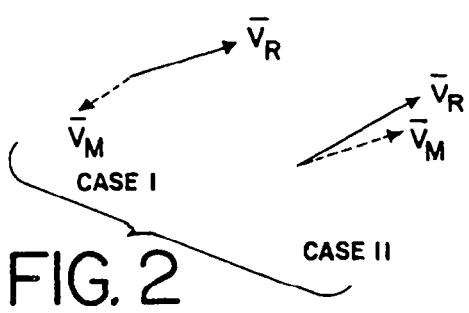
FIG. 2 is a graphical representation of two different example motion comparisons.

FIG. 2 shows two different examples of comparing a detected motion to a reference motion. In case one, the reference motion, $\vec{V}_r$, is a two-dimensional vector extending to the right as shown in the figure at about 15° above horizontal. Case 2 shows the same reference motion vector. The difference between case 1 and case 2 is the current or detected motion vector, $\vec{V}_m$. In case 1, the current motion vector, $\vec{V}_m$, is to the left and below horizontal by about 20°. The current motion vector in case 2 is to the right and about 10° above horizontal. The amplitude of the current motion vector in case 1 is much shorter than case 2. The difference in motion in case 1 is drastic, suggesting defective operation of the tissue. The difference in current motion and the reference motion in case 2 is little, suggesting expected, continued or healthy motion of the tissue. By detecting a difference between the reference motion and the detected, current motion, diagnostic information may be conveniently provided to the user.

The display 16 is a CRT, monitor, LCD, projector, plasma screen, combinations thereof or other now known or later developed display device. The display 16 receives the difference information or other information derived from the difference for displaying to the user. A two-dimensional image, a three-dimensional representation, a quantity, a graph or other image indicating the difference for one or more tissue locations is generated on the display 16.

Figure 3:
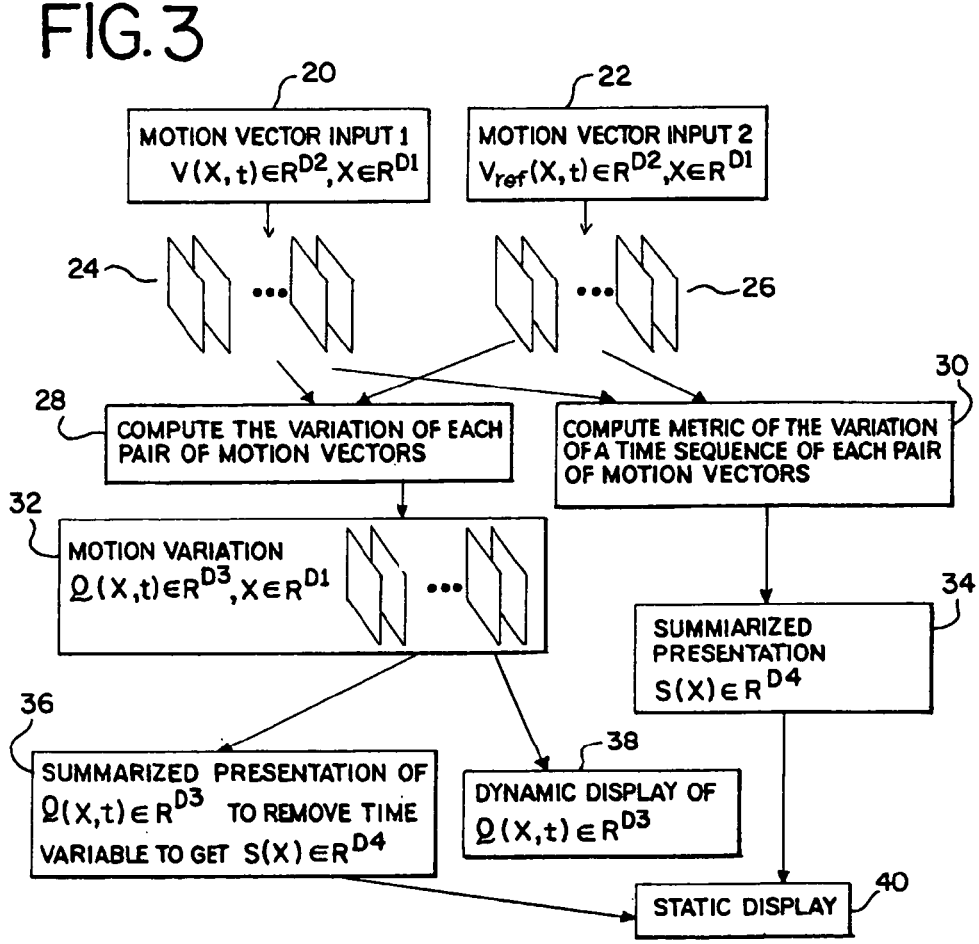
FIG. 3 is a flowchart diagram of one embodiment of a method for displaying tissue motion information.

FIG. 3 shows one embodiment of a method for displaying tissue motion information. The method is implemented using the system 10 of FIG. 1 or a different system. Additional, different or fewer acts may be provided in the same or different order. For example, acts 20, 22, 28 and 32 are provided without other acts. As another example, a single one of the display acts 38 or 40 is provided. As another example, one or no of the presentation acts 34, 36 are provided. As yet another example, acts 28 or 30 are provided without the other of act 30 or 28.

The acts of FIG. 3 are performed automatically by one or more processors in an imaging mode. Once a user configures an imaging system, the determination of motion vectors comparison and identification of differences due to the comparison are performed by processors with limited or no user input. For example, user input is provided for selecting a tissue region. The processor and associated instructions in software or firmware then automatically determine motion associated with the tissue region, compare the motion to a reference motion, and determine a difference in motion. The display is also automatically generated. An image varies as a function of the differences in motion or the associated comparison rather than providing for a mere subjective analysis by a human comparison.

In act 20, a motion characteristic of tissue within a body is determined. The motion characteristic is estimated from image intensity data, displacement data, velocity data, strain data, strain rate data, combinations thereof, or other now known or later developed medical diagnostic imaging data. The data may represent one-dimensional, two-dimensional or three-dimensional regions. Data sets representing a region or tissue at two different times are acquired. For example, the tissue is scanned with ultrasound energy at two different times or during a repeating interval to acquire a sequence of associated images or sets of data.

To determine a motion characteristic, a tissue position is tracked between data associated with different times. The tissue position to be tracked may be associated with a single location (e.g., pixel) or a region of interest. The tissue location may be automatically identified using an algorithm, such as border detection algorithms given a known tissue region for imaging, or may be identified in response to user input, such as user indication of one more points to identify a point, line or region of interest. For three-dimensional imaging, a tissue region of interest may be a surface, such as the endocardium or epicardium of the heart. More than one tissue location may be identified, such as a plurality of regions on a same tissue structure (e.g., seven or other number of segmented regions along a myocardial wall).

Using the identified location, a region around an identified location or both the identified location and a region around the identified location in one image, motion is determined by tracking the tissue location to a subsequent image. Tracking is performed by using a minimum sum of absolute difference, pattern comparison, motion estimated by velocity information, correlation, combinations thereof or other now known or later developed motion tracking techniques for one-, two- or three-dimensional image data to determine a translation, rotation or both translation and rotation. For example, motion tracking disclosed in U.S. Patent Application Publication Nos. 20040064036, 20040254440, and 20050096543 (attorney reference number 2003P14824US01); U.S. Pat. Nos. 6,527,717 and 6,193,660; and/or Robust Real-Time Myocardial Border Tracking for Echocardiography: An Information Fusion Approach, IEEE Trans. TMI Vol. 23 No. 7, is used. The disclosures of the above referenced patent publications and patents are incorporated herein by reference. The motion is tracked between sequential images in a sequence of images, but motion, between non-temporally adjacent images within a sequence may also be used. Techniques specifically for tracking motion in a particular type of tissue, such as cardiac wall motion, may be used.

An one-, two- or three-dimensional vector is determined as a function of the tracking. The vector has an associated amplitude and angle. The amplitude, angle or both amplitude and angle are determined as the motion characteristic. Other motion characteristics may alternatively or additionally be identified, such as a rotation. The identified one-, two- or three-dimensional vector information may be estimated, such as selecting a motion associated with a best match or a match meeting a threshold criteria. As shown in FIG. 3 in act 20, a motion vector is represented by V(X,t) where V is the vector, X is a location, t is time. $R^{D1}$ and $R^{D2}$ represent dimensions.

In act 22, a motion vector associated with a same or similar location X in a reference set is acquired. The reference motion is determined in a same or different way as the detected motion in act 20. The motion vector is pre-calculated for known or expected tissue locations or is determined in real-time with the determination of the detected motion vector in act 20. The reference motion characteristic is amplitude, angle, orientation, rotation, combinations thereof or other characteristic of motion matched to the characteristic of motion determined in act 20.

The reference motion characteristic is based on a reference data set. In one embodiment, the referenced data set is a model. For example, a dynamic model is based on a mathematical representation, a database or combinations thereof. The model represents either healthy motion or motion associated with one or more defects. In an alternative embodiment, the reference motion characteristic is based on a baseline data set. A patient is scanned to acquire a sequence of images associated with a region of interest before application of physical or pharmaceutical tests. For example, a baseline image set is acquired prior to a stress echo or other heart-based pharmaceutical tests. In another embodiment, the baseline is a previously acquired data set, such as from a last or previous examination, with or without application of a specific test. Baseline characteristics may be monitored as a function of time, such as years. In yet another embodiment, the reference motion characteristic is determined from the same data used as determining the motion characteristic in act 20 but at a different tissue location. For example, a reference motion is derived from an opposing cardiac wall. After applying any estimated inverse or other alteration in direction or amplitude, the reference from one tissue location may be used for comparing to the operation or movement of a tissue at another location with similar expected motion or motion that differs in a known or expected way.

For periodic motion, the detected motion characteristic and the reference motion characteristic are temporally aligned. One or more images associated with the determination of the motion characteristic are temporally aligned with one or more images associated with the reference motion in acts 24 and 26. The synchronization of two- or three-dimensional data sequences is performed using an ECG signal. Alternatively, other periodic indicators, such as velocity data, are used to identify the relative location of data within a cyclical sequence. Motion vectors within a threshold amount of time of each other during a repeating cycle may be used for a comparison. Alternatively, data is interpolated within a same cycle, such as a heartbeat interval, for determining motion at a same time within the cycle for a current sequence and the reference sequence. U.S. Pat. No. 6,673,017, the disclosure of which is incorporated herein by reference, discloses interpolation of data within a heart cycle. Temporal alignment may alternatively or additionally be provided for other cycles, such as the breathing cycle.

The image or image data associated with the detected motion characteristic is spatially registered with the image or image data associated with the reference motion characteristic in acts 24 and 26. For example, the data sequences are processed to register spatial relationships between the current data and the reference data using the geometry of the organ, such as a contour shape or shell shape, and/or using landmarks. The contour or landmarks may be entered by a user or automatically determined. For example, boundary detection algorithms identify contours associated with expected structures. The contours of the temporally aligned images are then compared. An amount of rotation to provide an optimal, best or sufficient match in two-or three-dimensions is determined using the minimum sum of absolute differences, correlation or other matching techniques. Scaling may alternatively or additionally be used, such as interpolating to provide contours on a similar or same scale. A scale may be set as a function of configuration of the imaging system, such as selecting an identified depth. The user adjusts real-time scanning to correspond to the reference set to provide similar or same scale.

The motion characteristic may be altered as a function of the spatial alignment. For example, the spatial alignment may indicate a lesser or greater amplitude or angle of motion between two images within a sequence. Alternatively, spatial alignment is performed prior to determining the current motion vector. In yet another alternative embodiment, the spatial alignment is used to identify the tissue location within the reference motion set for which the detected motion is relevant.

In act 28, the current motion characteristic is compared to the reference motion characteristic. A comparison is performed after any spatial and/or temporal registration. For three-dimensional imaging, the data sets for the current motion vector and the reference motion vector are reconstructed to a similar or same three-dimensional grid. Alternatively, data is tracked and compared in an acquisition format. For automatic comparison, a variation or difference is computed. "Difference" is used herein to indicate a general metric of similarity with or without a specific mathematical difference operation, such as using a ratio. In act 30, a metric is computed as a function of the comparison. For example, a metric of variation in the comparison as a function of time is determined. A maximum variation, minimum variation, variance or other characteristic of the comparison of motion vectors as a function of time is determined. Correlation, magnitude change or time delay may be calculated from the comparison of motion vectors as a function of time.

In act 32, the difference is determined as a function of the comparison. The difference is represented by Q. The difference is computed as a difference in amplitude, angle, orientation or combinations thereof. Other differences in motion vectors may be calculated, such as a difference vector. For example, a difference is a ratio of lengths or amplitudes of vectors. The difference is provided along one-, two- or three dimensions. The difference may be calculated along a single dimension of a multi-dimensional vector. The difference may have a dimension that is different from the dimensions of the motion vectors. For instance, Q(X,t) may be an angle between the motion vectors, a relative amplitude of the motion vectors or a difference (subtraction) in motion. The difference may be weighted as a function of differences in spatial or temporal offsets. For example, where the current motion vector is determined between two images acquired at twenty milliseconds apart but the reference motion vector associated with images separated by thirty milliseconds, the difference may be weighted by a ⅔weight. Other offset adjustments may be provided.

The determination of the motion characteristics, comparison and determination of the difference may be performed for each of a plurality of locations at a substantially same time. For example, a cardiac wall is divided into a plurality of segments. Motion associated with each of the segments is then tracked, compared and an associated difference determined. As another example, a motion vector is calculated for each point location, such as each pixel, separately for a region of interest. In alternative embodiments, a single location is tracked and compared for each region. Where a sequence of image represents tissue over a plurality of cyclical cycles, the motion associated with a given location at a given time within the cycle may be calculated in each of the sequences and averaged or otherwise combined, such as selecting a minimum or maximum.

In act 34, a summarized presentation is generated. A summarized presentation may include an identified quantity or quantities, a graph, a graphical representation or other indication of difference in motion as a function of time. In yet another embodiment, the summary is a chart of the differences in motion for each of a plurality of locations at each plurality of times. The differences may be divided into different characteristics, such as differences in amplitude, differences in angles, differences in orientations or other differences. Any metric resulting from the comparison of motion vectors at a given time or as a function of time is summarized.

In act 36, a summarized presentation as a function of time similar to, the same as or different than described above for act 34 is performed. For example, two different paths for two different outputs are provided. In the path including acts 32, 36 and 38, dynamic display and calculation of motion information is provided as well as calculation of metrics of the variation of the time sequence for each comparison of motion of the vectors. Static display 40 is the result of the summary presentation of acts 34 and 36. The other path represented by acts 30, 34 and 40 includes determination of static information but without a corresponding dynamic display of act 38.

In act 38, the difference information from act 32 is dynamically displayed. As the difference information is calculated during real-time imaging or playback, information is displayed as a function of the difference information in an ongoing basis or also in real-time. In act 40, a static display is provided. The static display is a review or non-real-time display. The display of acts 38 and/or acts 40 may take the same or different forms. For example, qualitative or quantitative displays are generated. For qualitative displays, one-, two-, or three-dimensional images are modulated as a function of the difference information. For example, locations associated with a given comparison are modulated in color, grayscale or both color and grayscale as a function of the corresponding difference. In the segmented heart wall embodiments discussed above, the pixel locations associated with each segment are modulated in a similar or same way. Alternatively, the modulation is interpolated between the centers of each segment for determining the modulations for locations between or within the two segments.

The comparison or difference information may be used to generate an image, such as using a difference characteristic, such as the ratio of magnitudes and/or angles as the basic modulation for a grayscale or color without combination with other information, such as B-mode image information. Alternatively, the difference information is used to modulate pixels overlaid on a B-mode, color or both color and B-mode image. Different difference metrics may be used in different ways, such as using an angle difference to represent hue and a difference in amplitude to modulate saturation. In one embodiment, a blue color represents the angle zero and a red color represents an angle of 180°. Color variations in between blue and red represent other angles.

As an alternative to direct modulation, a difference is input to a lookup table. A lookup table implements a linear or non-linear function for output values. For example, a given output value is provided for a range of differences. A different value is output for each of different ranges of differences. One range may represent similar motions, another range represents slightly different motion, and other ranges represent other relative amounts of differences. The relative amounts of differences are then used to modulate the display value or determine a display quantity or text. By providing a fewer number of steps or variations, a user may more immediately recognize differences of concern.

Additionally or alternatively, a value, a graph or both a value and a graph are displayed as a function of the difference or a comparison. The value may be a calculated function, such as the actual difference, a minimum, a maximum, an average, a correlation or other metric. A graph may include a difference or other metric as a function of time, a graphic representation of different vectors, such as shown in FIG. 2 or other graphical information. In one embodiment, a static image is provided with numerical values or difference vectors overlaid on top of the image for representing difference at a particular time, a metric as a function of a plurality of times or other comparison information.

The functions, acts or tasks illustrated in the figures or described above are performed by a programmed processor executing instructions stored in or on a computer-readable storage medium. The functions, acts or tasks are independent of the particular type of instructions set, storage medium, processor or processing strategy and may be performed by software, hardware, integrated circuits, firmware, microcode and the like, operating alone or in combination. Likewise, processing strategies may include multi-processing, multi-tasking, parallel processing and the like. Computer-readable storage medium include various types of volatile and non-volatile storage media, including but not limited to random access memory, read-only memory, programmable read-only memory, electrically programmable read-only memory, electrically erasable read-only memory, flash memory, magnetic tape or disk, optical media and the like. The instructions may be stored as part of any of the software, hardware, integrated circuits, firmware, microcode and the like. In one embodiment, the instructions are stored on a removable media device for reading by a medical diagnostic imaging system. The image system uploads the instructions for performing the acts discussed herein. In another embodiment, the instructions are stored in a remote location for transfer through a computer network or over telephone lines to an imaging system. In yet other embodiments, the instructions are stored within the imaging system on a hard drive, random access memory, cache memory, buffer, removable media or other device.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for displaying tissue motion information, the method comprising:
determining, with an ultrasound imaging system, a first motion of tissue within a body of a patient;
comparing the first motion to a first reference motion using respective first detected and reference motion characteristics, wherein the first reference motion characteristic is a modeled characteristic of a dynamic model based on a mathematical representation, the dynamic model comprising a motion vector, which is a function of location and time;

determining a difference as a function of the comparison such that a deviation of the first motion of the tissue from the first reference motion is represented by the difference; and displaying, on a display of the ultrasound imaging system, information as a function of the difference, the information being displayed representing the deviation.

2. The method of claim 1 wherein determining the first motion comprises:

scanning the tissue with ultrasound at different times; and tracking tissue position at the different times.

3. The method of claim 1 wherein determining the first motion, comparing, determining the difference and displaying are performed automatically by one or more processors in an imaging mode.

4. The method of claim 1 wherein determining the first motion comprises determining a two-dimensional vector.

5. The method of claim 1 wherein determining the first motion comprises determining a three-dimensional vector.

6. The method of claim 1 wherein determining the first motion comprises determining an amplitude, an angle or both an amplitude and an angle of motion.

7. The method of claim 1 wherein determining the difference comprises determining a difference in amplitude, angle or both amplitude and angle.

8. The method of claim 1 wherein displaying information as a function of the difference comprises modulating two or three dimensional image color, gray scale or both color and gray scale as a function of the difference.

9. The method of claim 1 wherein displaying information as a function of the difference comprises displaying a value, a graph or both a value and a graph as a function of the difference.

10. The method of claim 1 wherein displaying information as a function of the difference comprises displaying as a function of the difference relative to at least two different ranges of difference values.

11. The method of claim 1 further comprising:

spatially registering a first image associated with the first tissue motion with a second image associated with the first reference motion;

wherein comparing is performed after the spatial registration.

12. The method of claim 1 further comprising:

temporally aligning a first image associated with the first tissue motion with a second image associated with the first reference motion, the second image being in a sequence of reference images.

13. The method of claim 1 further comprising:

repeating the determining the first motion characteristic, comparing, and determining the difference for each of a plurality of locations at a substantially same time;

wherein displaying comprises displaying as a function of differences for each of the plurality of locations in a same image.

14. A system for displaying tissue motion information, the system comprising:

an imaging system processor configured to determine a first motion of tissue within a body, compare the first motion to a first reference motion using respective first detected and reference motion characteristics, the reference motion characteristics being from a mathematical or database-based dynamic model of motion, the dynamic model comprising a motion vector, which is a function of location and time, and determine a difference as a function of the comparison such that a deviation of the first motion of the tissue from the first reference motion is represented by the difference; and a display of the imaging system, the display configured to display information as a function of the difference, the information being displayed representing the deviation.

15. The system of claim 14 comprising a medical diagnostic ultrasound system.

16. A non-transitory computer readable storage medium having stored therein data representing instructions executable by a programmed processor for displaying tissue motion information, the storage medium comprising instructions for:

determining a first motion of tissue within a body with of a patient with ultrasound data acquired at different times from the patient;

comparing the first motion to a first reference motion using respective first detected and reference motion characteristics, wherein the first reference motion is a modeled characteristic from a dynamic model, the dynamic model comprising a motion vector, which is a function of location and time;

determining a difference as a function of the comparison such that a deviation of the first motion of the tissue from the first reference motion is represented by the difference; and displaying the information as a function of the difference, the information being displayed representing the deviation.

17. The non-transitory computer readable storage medium of claim 16 wherein determining the first motion comprises determining a two-or three-dimensional vector.

18. The non-transitory computer readable storage medium of claim 16 wherein determining the first motion comprises determining an amplitude, an angle or both an amplitude and an angle of motion, and wherein determining the difference comprises determining a difference in amplitude, angle or both amplitude and angle.

19. The non-transitory computer readable storage medium of claim 16 wherein displaying information as a function of the difference comprises modulating two or three dimensional image color, gray scale or both color and gray scale as a function of the difference.

20. The non-transitory computer readable storage medium of claim 16 wherein displaying information as a function of the difference comprises displaying a value, a graph or both a value and a graph as a function of the difference.

21. The non-transitory computer readable storage medium of claim 16 wherein displaying information as a function of the difference comprises displaying as a function of the difference relative to at least two different ranges of difference values.

22. The non-transitory computer readable storage medium of claim 16 further comprising instructions for:

temporally aligning a first image associated with the first tissue motion with a second image associated with the first reference motion, the second image being in a sequence of reference images; and spatially registering the first image with the second image;

wherein comparing is performed after the spatial registration.

23. The non-transitory computer readable storage medium of claim 16 further comprising instructions for:

repeating the determining the first motion characteristic, comparing, and determining the difference for each of a plurality of locations at a substantially same time;

wherein displaying comprises displaying as a function of differences for each of the plurality of locations in a same image.

\* \* \* \* \*